US011478180B2

(12) United States Patent
Whittaker et al.

(10) Patent No.: US 11,478,180 B2
(45) Date of Patent: Oct. 25, 2022

(54) PROBE RESPONSE SIGNALS

(71) Applicant: University of Newcastle Upon Tyne, Newcastle upon Tyne (GB)

(72) Inventors: Roger Whittaker, Newcastle upon Tyne (GB); Anthony O'Neill, Newcastle upon Tyne (GB); Stuart Baker, Newcastle upon Tyne (GB); Bashar Awwad Shiekh Hasan, Newcastle upon Tyne (GB); Enrique Escobedo-Cousin, Newcastle upon Tyne (GB)

(73) Assignee: University of Newcastle Upon Tyne, Newcastle upon Tyne (GB)

( * ) Notice: Subject to any disclaimer, the term of this patent is extended or adjusted under 35 U.S.C. 154(b) by 1231 days.

(21) Appl. No.: 15/768,460

(22) PCT Filed: Oct. 12, 2016

(86) PCT No.: PCT/GB2016/053152
§ 371 (c)(1),
(2) Date: Apr. 13, 2018

(87) PCT Pub. No.: WO2017/064477
PCT Pub. Date: Apr. 20, 2017

(65) Prior Publication Data
US 2018/0289277 A1 Oct. 11, 2018

(30) Foreign Application Priority Data
Oct. 14, 2015 (GB) ..................... 1518205

(51) Int. Cl.
*A61B 5/00* (2006.01)
*A61B 18/14* (2006.01)
(Continued)

(52) U.S. Cl.
CPC ............... *A61B 5/296* (2021.01); *A61B 5/30* (2021.01); *A61B 5/4041* (2013.01);
(Continued)

(58) Field of Classification Search
CPC ... A61B 5/4041; A61B 5/4893; A61B 5/6848; A61B 5/25; A61B 5/262; A61B 5/6824;
(Continued)

(56) References Cited

U.S. PATENT DOCUMENTS 3,313,293 A 4/1967 Chesebrough et al.
4,630,611 A 12/1986 King
(Continued)

FOREIGN PATENT DOCUMENTS

EP 1894522 B1 3/2008
EP 2266484 A4 12/2010
(Continued)

OTHER PUBLICATIONS

International Search Report and Written Opinion issued in PCT/GB2016/053152 dated Feb. 1, 2017. 17 pages.
(Continued)

*Primary Examiner* — Eun Hwa Kim
(74) *Attorney, Agent, or Firm* — Sheridan Ross P.C.

(57) ABSTRACT

A method and apparatus are disclosed for simultaneously providing a plurality of probe response signals indicative of electrical activity at a respective plurality of locations in a patient. The apparatus comprises a rigid needle shaft element comprising a piercing tip and a substrate supporting a plurality of electrode tracks, secured to the needle shaft element and extending along the shaft element away from the piercing tip. Each electrode track extends from a sensing end region arranged for providing a respective probe response signal responsive to localised electrical activity, along the region of the substrate, to a respective bond pad
(Continued)

connection region. Recording surface regions of the plurality of electrode tracks are spaced apart in a plurality of substantially linear spaced apart configurations along the substrate.

18 Claims, 17 Drawing Sheets

(51) Int. Cl.
*A61B 5/296* (2021.01)
*A61B 5/30* (2021.01)
*A61B 18/00* (2006.01)

(52) U.S. Cl.
CPC .......... *A61B 5/4893* (2013.01); *A61B 5/6848* (2013.01); *A61B 18/1477* (2013.01); *A61B 18/1492* (2013.01); *A61B 2018/00839* (2013.01); *A61B 2018/1425* (2013.01); *A61B 2562/04* (2013.01)

(58) Field of Classification Search
CPC ... A61B 5/6825; A61B 5/6828; A61B 5/6829; A61B 5/685; A61B 2562/04; A61B 2562/043; A61B 2562/046
See application file for complete search history.

(56) References Cited

U.S. PATENT DOCUMENTS

| | | | |
|---|---|---|---|
| 5,397,344 A | 3/1995 | Garfield et al. | |
| 6,584,347 B1 | 6/2003 | Sinderby | |
| 7,941,202 B2* | 5/2011 | Hetke | A61B 5/24 600/377 |
| 9,113,912 B1 | 8/2015 | Mehta et al. | |
| 9,351,659 B2 | 5/2016 | Gilmore et al. | |
| 2004/0121619 A1 | 6/2004 | Yokoi et al. | |
| 2007/0219551 A1* | 9/2007 | Honour | A61B 5/6852 606/41 |
| 2008/0139911 A1* | 6/2008 | Chandrasekaran | A61B 5/25 600/382 |
| 2008/0140152 A1* | 6/2008 | Imran | A61N 1/0556 607/46 |
| 2011/0093052 A1* | 4/2011 | Anderson | A61N 1/0534 29/874 |
| 2011/0288391 A1 | 11/2011 | Rao et al. | |
| 2013/0018247 A1 | 1/2013 | Glenn et al. | |
| 2013/0245733 A1* | 9/2013 | Yomtov | A61N 1/36125 607/116 |
| 2014/0114168 A1* | 4/2014 | Block | A61M 29/00 600/393 |
| 2014/0180361 A1 | 6/2014 | Burdick et al. | |
| 2014/0180631 A1 | 6/2014 | Papakostas | |

FOREIGN PATENT DOCUMENTS

| | | |
|---|---|---|
| WO | WO9822021 A4 | 5/1998 |
| WO | WO2013034923 A1 | 3/2013 |
| WO | 2014189077 A1 | 11/2014 |

OTHER PUBLICATIONS

Marco Gazzoni et al. "Quantifying Forearm Muscle Activity during Wrist and Finger Movements by Means of Multi-Channel Electromyography." PLOS One. vol. 9, Issue 10. pp. 1-11. Oct. 2014.

Ajith Sivadasan et al. "Utility of Multi-Channel Surface Electromyography in Assessment of Focal Hand Dystonia." Muscle & Nerve. pp. 415-422. Sep. 2013.

Antonietta Stango et al. "Spatial correlation of high density EMG signals provides features robust to electrode number and shift in pattern recognition for myocontrol." IEEE Transactions on Neural Systems and Rehabilitation Engineering, vol. 23, No. 2. pp. 189-198. Mar. 2015.

* cited by examiner

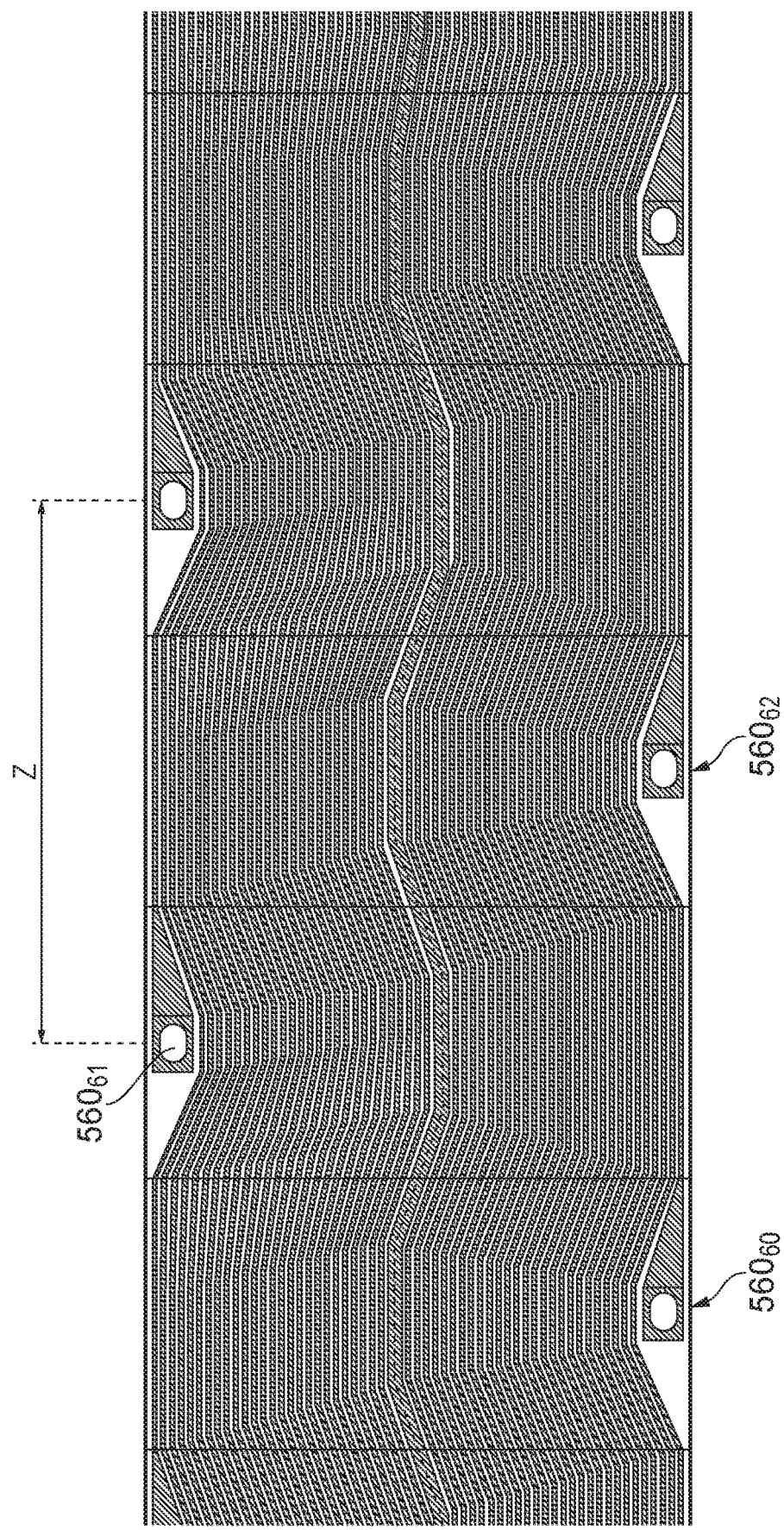

Si wafer

Al layer

Parylene-C

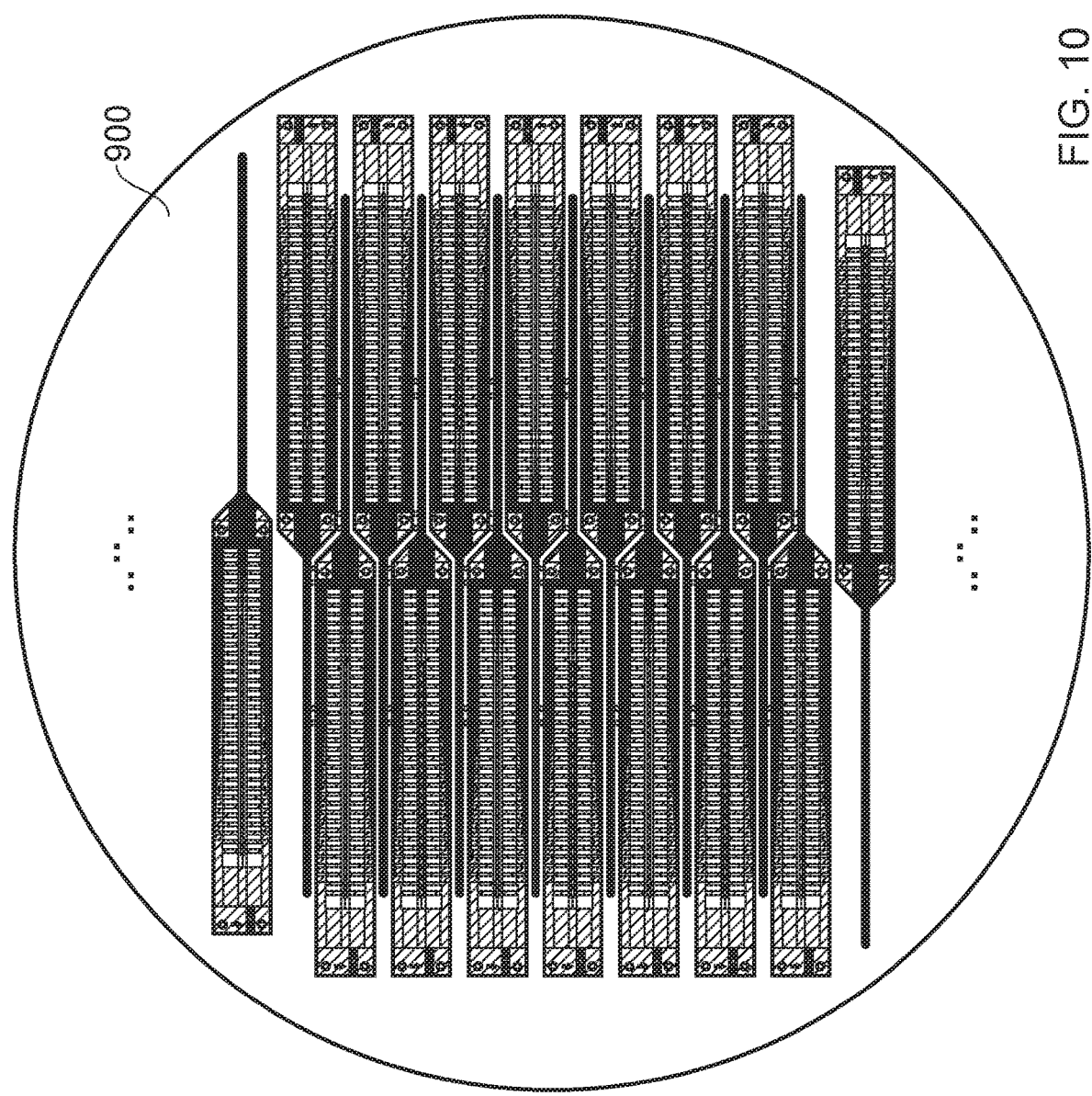

PROBE RESPONSE SIGNALS

CROSS-REFERENCE TO RELATED APPLICATIONS

This application is a national stage application under 35 U.S.C. § 371 and claims the benefit of PCT Application No. PCT/GB2016/053152 having an international filing date of 12 Oct. 2016, which designated the United States, which PCT application claimed the benefit of Great Britain Patent Application No. 1518205.8 filed 14 Oct. 2015, the disclosures of each of which are incorporated herein by reference in their entireties.

FIELD

The present invention relates to a method and apparatus for simultaneously providing a plurality of probe response signals indicative of electrical activity at a respective plurality of locations in a patient. In particular, but not exclusively, the present invention relates to needle electromyography and microneurography and to a needle and method of manufacturing a needle that can be used in such techniques to simultaneously provide probe response signals from multiple locations in a patient at a single needle site. The probe signals can optionally be used to help diagnose disease.

BACKGROUND

Many different techniques and apparatus for use in medical techniques are known for providing useful data as to the proper functioning of a human or animal body.

For example microneurography (MNG) is a known medicine technique. This is a neurophysical method employed to visualise and record normal or abnormal traffic of nerve impulses that are conducted in peripheral nerves of waking human or animal subjects. The method can successfully be employed to reveal functional properties of a number of neural systems, e.g. sensory systems relating to touch, pain and muscle sense, as well as sympathetic activity controlling the constriction state of blood vessels.

Another example is electromyography (EMG) which is an electrodiagnostic medicine technique for evaluating and recording the electrical activity produced by skeletal muscles. EMG is performed using an instrument called an electromyograph to produce a record called an electromyogram. An electromyograph detects the electrical potential generated by muscle cells when these cells are electrically or neurologically activated. The signals can subsequently be analysed to detect medical abnormalities, activation level or recruitment order or to analyse the biomechanics of human or animal movement.

Needle electromyography (EMG) is an important tool in the diagnosis of neuromuscular diseases. For motor neuron disease (MND), and certain forms of myasthenia gravis, it is the only test available. Accurate, early diagnosis is essential for the instigation of appropriate therapy.

Conventional EMG measures electrical activity generated within skeletal muscle. Muscles consist of thousands of cylindrical muscle fibres in a body arranged in parallel. The smallest unit of voluntary muscle control is the motor unit. Each motor unit comprises one motor nerve axon and the several hundred muscle fibres it supplies. Motor units overlap within the muscle; fibres in one unit interdigitate with up to ten adjacent units. Human motor units can extend over 5-10 mm diameter, with muscle fibres spaced ~200 μm apart.

Various diseases cause different motor unit structure changes. The progressive loss of motor axons in MND leaves the muscle fibres in their motor units without a nerve supply. Surviving motor axons re-establish connection to some of these fibres to produce large, densely packed motor units. Conversely, primary muscle diseases, such as polymyositis, cause unequal fibre atrophy, leading to small motor units with greater variability in fibre diameter. In diseases affecting the nerve-muscle junction, e.g. myasthenia gravis, variability in muscle fibre firing increases. It is these changes in motor unit size, structure and stability that form the basis of EMG diagnosis.

Conventional EMG uses a concentric metal needle (typically 4 cm long by 0.3 mm diameter) consisting of a central wire, separated from the shaft by an insulating layer. This is inserted through the skin into a muscle. A fundamental limitation is that only a single recording surface at the needle tip is used. This samples an area of approximately 1 mm radius, far smaller than a typical motor unit. The resulting composite signal is therefore derived from a small subset of the muscle fibres in the unit, their distribution within that unit is unknown, and furthermore, several overlapping motor units contribute to the signal. The EMG signal is displayed on a monitor and the electromyographer (human operator) attempts to infer the underlying motor unit structure in real time. Routine EMG interpretation is therefore highly subjective, and even in the most experienced hands, diagnostic accuracy is poor. Various quantitative techniques have been developed, but these all require off-line analysis, increasing the time needed for the study.

Conventionally even if the EMG signal is clearly abnormal, only a tiny volume of muscle is sampled at any one needle location site. Demonstrating a diffuse disorder such as MND requires the needle to be repositioned several times in each muscle. This increases the discomfort for the patient and the time taken for the study. Similarly, demonstrating a defect of neuromuscular transmission requires the measurement of jitter in multiple muscle fibres, typically requiring >1 hour of clinical time.

These limitations have long been recognised. In the 1970s primitive 16 channel multi-EMG needles were developed. Recordings were made from only one or two channels at a time, and the needle advanced by hand between successive needle location sites to produce an estimate of muscle fibre distribution. A similar known technique, scanning EMG, uses a single channel needle drawn slowly through the muscle using a stepper motor to produce an electrical cross section of a muscle. Both are technically demanding, take hours to perform, and thus have never entered routine clinical practice.

SUMMARY

It is an aim of the present invention to at least partly mitigate one or more of the above-mentioned problems.

It is an aim of certain embodiments of the present invention to provide a needle with multiple sensing positions which can be utilised to simultaneously take potential signal readings from multiple locations in a human or animal patient at a single needle location site.

It is an aim of certain embodiments of the present invention to provide a method of manufacturing a multi electrode supporting substrate which can be subsequently secured to a piercing needle and thereafter used for signal analysis in a human or animal patient.

It is an aim of certain embodiments of the present invention to provide a method of diagnosis via electromyography or microneurography or other needle based probing technique which can be utilised as a diagnostic tool with regard to human or animal patients.

According to a first aspect of the present invention there is provided apparatus for simultaneously providing a plurality of probe response signals indicative of electrical activity at a respective plurality of locations in a patient, comprising:

a rigid needle shaft element comprising a piercing tip; and
a substrate, supporting a plurality of electrode tracks, secured to the needle shaft element and extending along the shaft element away from the piercing tip; wherein each electrode track extends from a sensing end region arranged for providing a respective probe response signal responsive to localised electrical activity, along a region of the substrate to a respective bond pad connection region and recording surface regions of the plurality of electrode tracks are spaced apart in a plurality of substantially linear spaced apart configurations along the substrate.

Aptly the substrate is formed from a flexible material.

Aptly the substrate is bent at least partially around a cylindrical outer surface of the needle shaft element.

Aptly the substrate is bonded to an outer surface of the needle shaft element.

Aptly each electrode track comprises a connection track portion, that extends substantially parallel with an axis of the needle shaft element and the substrate, spaced apart from at least one adjacent connection track portion.

Aptly each electrode track further comprises a sensing track portion that extends substantially perpendicular to the connection track portion and inwardly towards an imaginary centre line extending along the centre of the substrate, an end of the sensing track portion comprising the sensing end region Aptly each electrode track comprises a fan out portion that turns away from an imaginary centre line of the substrate and extends towards an edge region of the substrate from a distal end of a respective connection track portion of the electrode track towards a respective bond pad connection.

Aptly each electrode track comprises a zig-zag shaped connection track portion that extends in a nested spaced apart configuration with at least one adjacent zig-zag shaped connection track portion.

Aptly each electrode track comprises a sensing track portion that extends from an end of a respective connection track portion of the electrode track and is substantially aligned in a common direction with the respective an end and has a width greater than or less than a width of said an end, a terminal end of the sensing track portion comprising the sensing end region.

Aptly each electrode track comprises a fan out portion that turns away from an imaginary centre line of the substrate and extends towards an edge region of the substrate from a distal end of a respective connection track portion of the electrode track towards a bond pad connection.

Aptly at least one reference electrode track including a terminal end portion and at least one reference electrode connection track portion.

Aptly the substrate and supported electrode tracks and needle shaft element are disposable as a single unit.

Aptly the substrate supports at least sixteen distinct spaced apart electrode tracks.

Aptly the substrate supports at least thirty two distinct spaced apart electrode tracks.

Aptly the substrate supports at least sixty four distinct spaced apart electrode tracks.

Aptly each electrode track comprises a metallic conductive pathway.

Aptly each electrode track comprises a tungsten titanium track.

Aptly each electrode track comprises an etched metallic deposition element.

Aptly the apparatus comprises an electromyography (EMG) needle.

Aptly a recording surface region of each electrode track is substantially circular and has a diameter of about around 40 to 60 µm.

Aptly each recording surface has a diameter of about around 50 µm.

Aptly each recording surface region is spaced apart in a substantially linear configuration along the substrate.

Aptly each recording surface region of the plurality of electrode tracks are spaced apart from an adjacent recording surface region by about around 150 to 250 µm and optionally by about around 200 µm.

Aptly each recording surface region of the plurality of electrode tracks are spaced apart in a respective one of two substantially linear configurations along the substrate.

Aptly each recording surface region in each linear configuration is spaced apart by about around 350 to 450 µm and each linear configuration of recording surface regions are spaced apart by about around 250 to 350 µm.

Aptly the apparatus comprises a microneurography needle.

Aptly a recording surface region of each electrode track has an area of about around 10-50 µm$^2$.

Aptly each recording surface is spaced apart in a substantially linear configuration along the substrate.

Aptly each recording surface region is spaced apart by about around 5 to 25 µm and optionally by about around 10 to 20 µm.

According to a second aspect of the present invention there is provided a method of manufacturing a flexible electrode array for securing to a needle shaft, comprising the steps of:

providing a base substrate layer over a sacrificial layer;
depositing a metallic layer over the base substrate layer;
selectively etching the metallic layer to provide a plurality of electrode tracks on the substrate layer;
depositing a cover substrate layer over the etched metallic layer prior to dissolving the sacrificial layer;
etching a plurality of electrode tracks each comprising a sensing track portion, an intermediate connection track portion and a fan out portion; and
dissolving the sacrificial layer to thereby provide a flexible substrate having a neck region and a body region supporting a plurality of electrode tracks.

According to a third aspect of the present invention there is provided a method of diagnosing at least one disease in a patient, comprising the steps of:

urging a needle through the skin of a patient at a needle location site;
via a plurality of electrode tracks comprising recording surface regions spaced apart in a plurality of substantially linear spaced apart configurations supported on a substrate secured on a needle shaft element of the needle, simultaneously providing a plurality of probe response signals each indicative of electric activity at a respective one of a plurality of sub-locations in the patient.

Aptly the method further comprises displaying at least one output trace on a display responsive to the probe response signal; and responsive to the output trace, determining a likelihood of one or more diseases.

Aptly the method further comprises providing a 2-D image of said probe signal in real time.

Aptly the method further comprises providing an image of a motor unit morphology and/or motor unit stability responsive to the probe signals.

Aptly the method further comprises simultaneously providing jitter recordings from multiple fibres in a patient at each needle location site.

Aptly the method further comprises simultaneously recording a measured voltage from a plurality of sub locations in the patient at each needle location site.

According to a fourth aspect of the present invention there is provided a method substantially as hereinbefore described with reference to the accompanying drawings.

According to a fifth aspect of the present invention there is provided apparatus constructed and arranged substantially as hereinbefore described with reference to the accompany drawings.

Certain embodiments of the present invention provide apparatus and/or a method for simultaneously providing a plurality of probe response signals indicative of electrical activity at a respective plurality of locations in a patient.

Certain embodiments of the present invention provide the ability to record the electrical activity produced by skeletal muscle fibres from an array of multiple recording surfaces of known location.

Certain embodiments of the present invention enable a relative signal strength of the electrical signals arriving at multiple sensors to accurately localise the muscle fibres in space.

Certain embodiments of the present invention enable/provide the localisation and distribution of muscle fibres as a diagnostic test in the investigation of diseases affecting the skeletal muscles and the motor nerves supplying those muscles.

Certain embodiments of the present invention provide the ability to simultaneously record the electrical activity produced by muscle fibres across several entire motor units removing the need to move a needle within a muscle.

Certain embodiments of present invention provide the ability to simultaneously record the time of firing of multiple individual muscle fibres within several different motor units and hence to rapidly calculate the stability of nerve-muscle impulse transmission ("jitter").

Certain embodiments of the present invention provide apparatus which is readily manufacturable and which can provide a disposable sensor able to determine electrical activity at a plurality of locations in a patient with a single needle position.

BRIEF DESCRIPTION OF THE DRAWINGS

Embodiments of the present invention will now be described hereinafter, by way of example only, with reference to the accompanying drawings in which:

FIG. 7 illustrates a region of electrode tracks having a zig-zag shape;

FIG. 10 illustrates how multiple substrates with respective electrode tracks can be manufactured from a common silicon wafer.

In the drawings like reference numerals refer to like parts.

DETAILED DESCRIPTION

Figure 1:
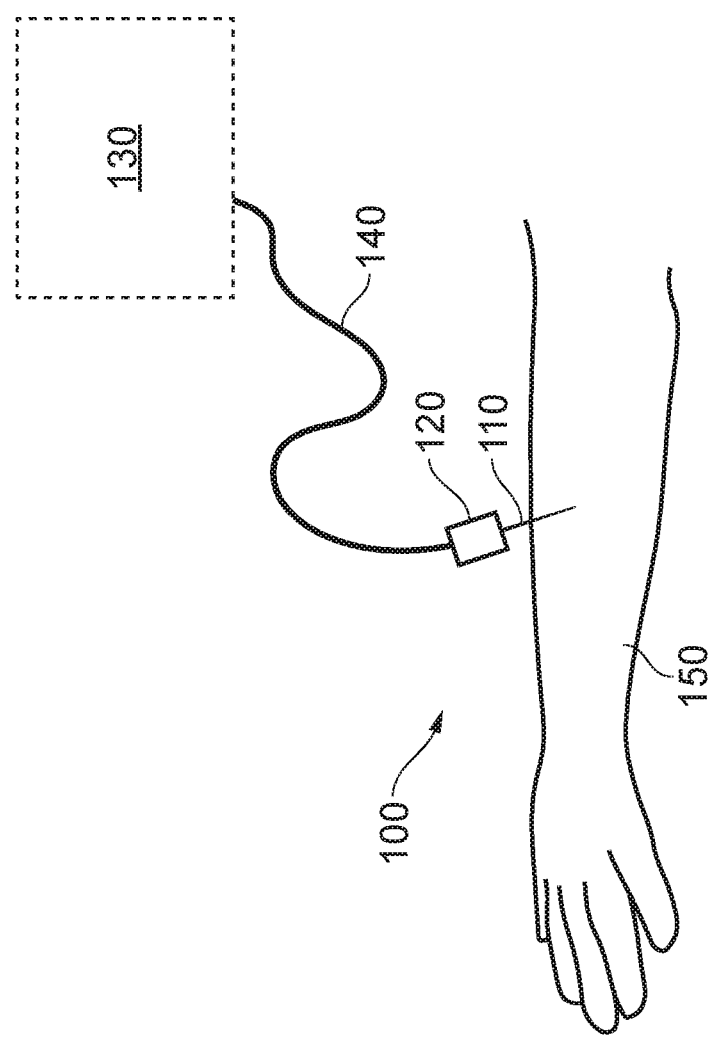
FIG. 1 illustrates a method of diagnosis being carried out on a human.

FIG. 1 illustrates how a sensor for simultaneously providing a plurality of probe response signals, indicative of electrical activity at a respective plurality of locations in a patient, can be used during a method of diagnosis on a human. It will be appreciated that certain embodiments of the present invention can be utilised with other mammals or animals. It will likewise be appreciated that certain embodiments of the present invention can be used to provide data indicative of electrical activity. That data can be utilised in real time or later to make informed decisions. Data may be displayed or merely manipulated to make decisions.

As illustrated in FIG. 1 a hand held (or alternatively machine operated) sensor 100 includes a needle 110 mounted to a housing body 120 which can be manipulated and thereby located by a health care professional. The device body 120 can be used like a handle and includes electronics and connections (described later) and these are connected to a remote monitoring/diagnostic station or data collection station illustrated in FIG. 1 via a dotted line 130. Optionally the remote station can include a display for displaying representation/signal traces associated with output from the sensor. It will be appreciated that if the hand held device 120 includes an internal power source then the wired connection 140 illustrated in FIG. 1 could optionally be a wireless connection.

FIG. 1 helps illustrate how a limb or other body portion of a human can be probed with the sensor 100. FIG. 1 illustrates an arm 150 and by using the device 100 electrical activity generated within skeletal muscle can be probed. The needle 110 illustrated in FIG. 1 is shown as already having been inserted at a desired location in the patient's arm 150. Such location of the sensor is achieved by a qualified user such as a doctor or nurse or in an automated fashion. Multiple signals from different locations in the patient can be obtained for each needle location. The needle itself may be repeatedly located at different positions.

The needle 110 of the device 100 illustrated in FIG. 1 is an electromyography (EMG) needle. It will be appreciated that according to certain other embodiments of the present invention the needle used can be a microneurography needle or other such probing instrument or the like.

Figure 2:
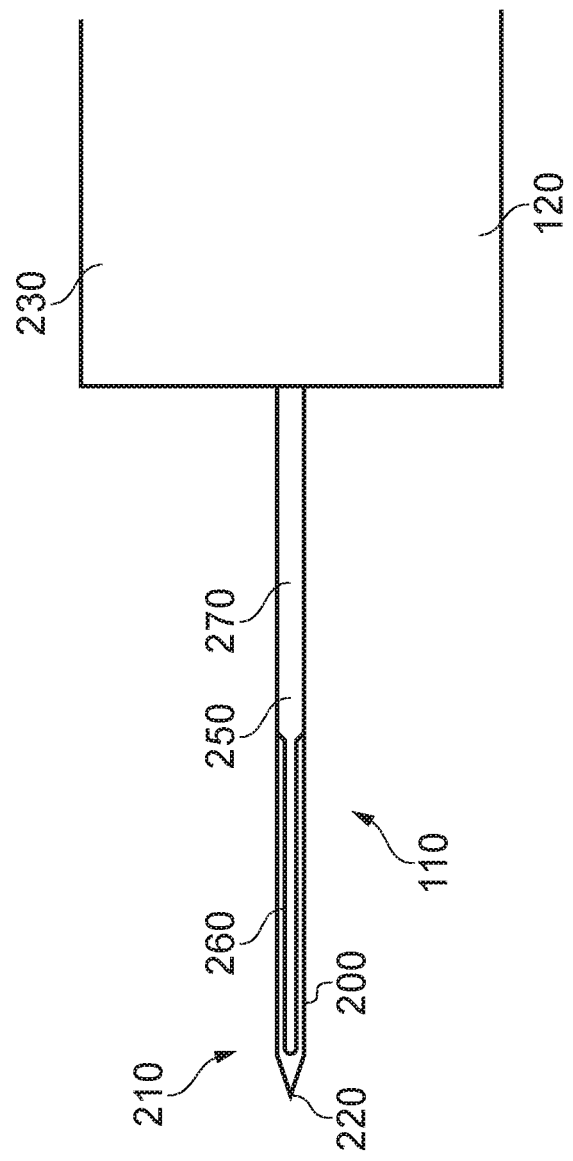
FIG. 2 illustrates a multi-electrode supporting substrate mounted on a needle.

FIG. 2 helps illustrate the needle 110 and housing body 120 of the EMG needle in more detail. As illustrated in FIG. 2 the needle includes a rigid shaft 200 which is a substantially cylindrical element having a cylindrical outer surface which terminates at an end region 210 with a piercing tip 220. Aptly for the illustrated EMG needle the diameter of the needle is about around 400-500 µm. It will be appreciated that for other uses a needle might optionally have other sizes. For example for a microneurography needle the diameter may be about around 40-60 µm. The needle body 200 extends into the housing 120. The housing has an outer surface 230 which can be manipulated by hand and which helps prevent ingress of contaminants. The housing contains connectors between the amplifier and ADC circuitry that provides outputs responsive to the sensed activity from each sensing point provided on the sensor.

As illustrated in FIG. 2 the rigid needle shaft, which terminates in the piercing tip 220, carries on the outer surface a substrate 250 which includes a narrow neck region 260 which extends away from the housing 120 towards the piercing tip of the needle. The substrate also includes a wider main body part region 270. A shoulder region is between the narrow neck and wide substrate body. Aptly the substrate is formed from a flexible material and can be bent at least partially (or wholly) around the cylindrical outer surface of the needle shaft. One side of the substrate is secured to the outer surface of the needle. Aptly the substrate is bonded via an adhesive or the like to the outer surface of the needle. Other techniques for securing the substrate in place with respect to the needle can of course be utilised. For example the substrate may be annealed to the needle material or held in place via one or more securing rings.

Figure 3:
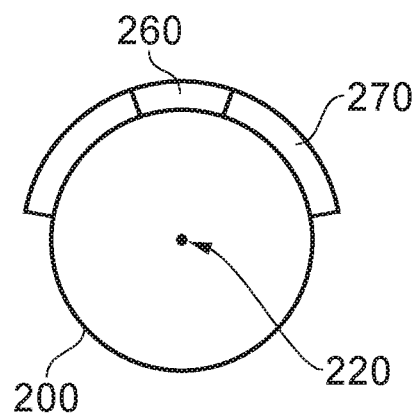
FIG. 3 illustrates another view of the multi electrode supporting substrate shown in FIG. 2 helping illustrate how this may be partially wrapped around the needle.

FIG. 3 helps illustrate a "head-on" view of the piercing tip 220 of the needle body and helps illustrate how the substrate 250 is partially wrapped around the outer surface 200 of the needle and fixed in place. FIG. 3 helps illustrate how the narrow neck 260 of the substrate extends longitudinally away from the housing (not shown) towards the tip of the needle. The remaining wider portion of the substrate 270 is illustrated wrapped around the needle and this extends away from the top (into the page) into the housing.

Figure 4:
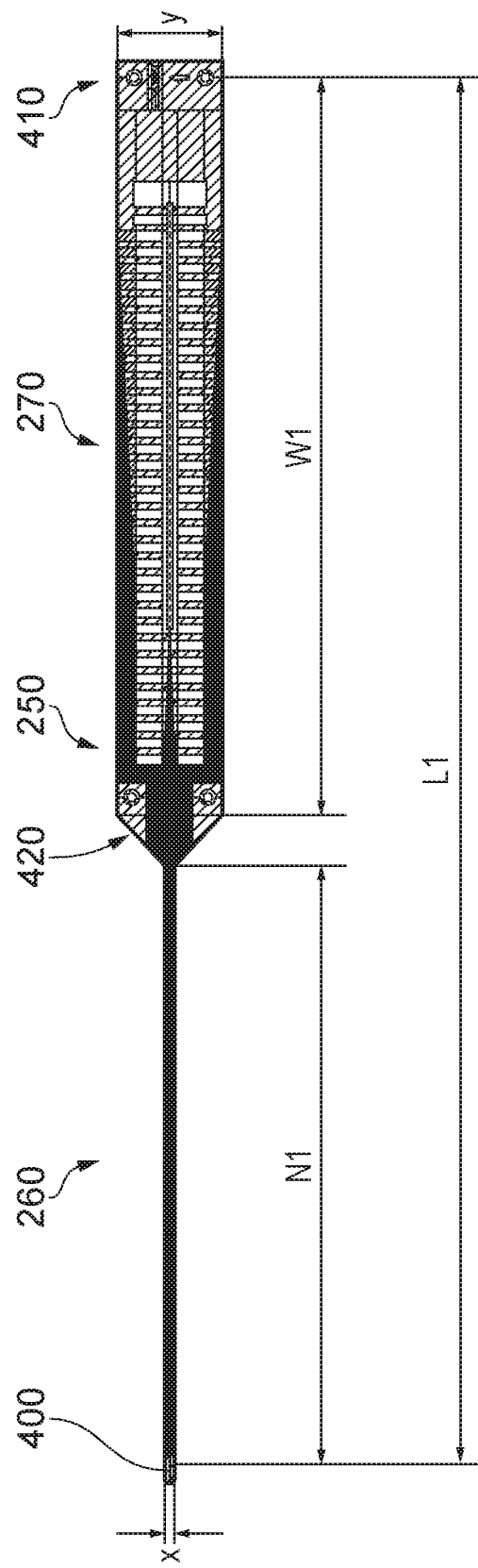
FIG. 4 illustrates the multi electrode supporting substrate in more detail.

FIG. 4 illustrates a substrate 250 in more detail in a "flat" format subsequent to manufacture and prior to mounting and securing on to a piercing needle. As illustrated in FIG. 4 the substrate has a narrow neck region 260 which includes a first substrate end 400. At a remaining substrate 410 end the substrate is flared out and has a greater width. The width x of the narrowed neck part of the substrate is approximately 50-500 µm. Aptly the width of the narrowed neck of the substrate is around 400 µm. By contrast the wider/thicker end of the substrate has a thickness y which is about around 300-1000 µm. Aptly the width of the thicker part of the substrate is around 400 µm. A shoulder or intermediate region 420 of the substrate flares outwardly moving from the narrowed neck part of the substrate towards the thicker main part. The overall length of the substrate from the end 400 of the narrow neck to the wide end 410 is illustrated with reference L1. Aptly this overall length of substrate is 50 mm. The overall length of the narrowed neck region of the substrate is illustrated with reference N1 which has an approximate length of 25 mm. The overall length of the wide portion of the substrate is illustrated in FIG. 4 with reference W1 which is around 30 mm.

The substrate illustrated in FIG. 4 is formed from a material which is flexible. That is to say the thickness of the substrate and material used for its manufacture are chosen so that the substrate to at least some extent can be wrapped around an outer surface of the needle. Aptly the substrate is flexible enough to be able to be wrapped around, and thus be closely associated with at least a quarter of a whole circumference of the outer surface of the needle. Aptly the substrate is flexible enough to be wrapped around a third or more of the whole of the outer circumference of the needle outer surface. Alternatively the substrate may be manufactured from a rigid material in which case the needle to which it is secured for use should have a flat chamfered surface along its length. Aptly the substrate is a parylene-C layer.

The substrate supports multiple electrode tracks which each extend from a sensing end of the electrode track on the narrow neck of the substrate, along at least a part of the substrate, to a respective bond pad on the main body part region 270 of the substrate. Aptly the electrode tracks are covered by a layer of parylene-C.

Figure 5:
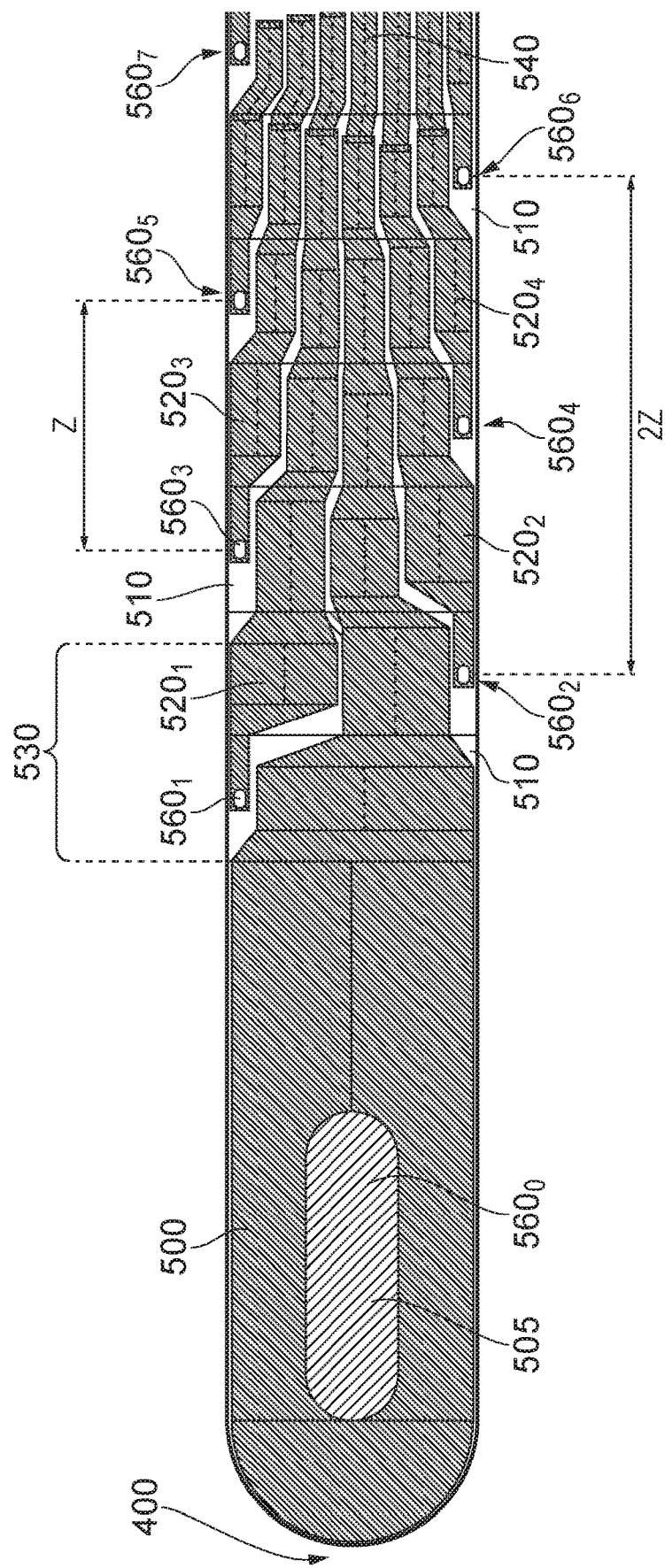
FIG. 5 illustrates a sensing end of a substrate that supports multiple electrode tracks.
Figure 6A:
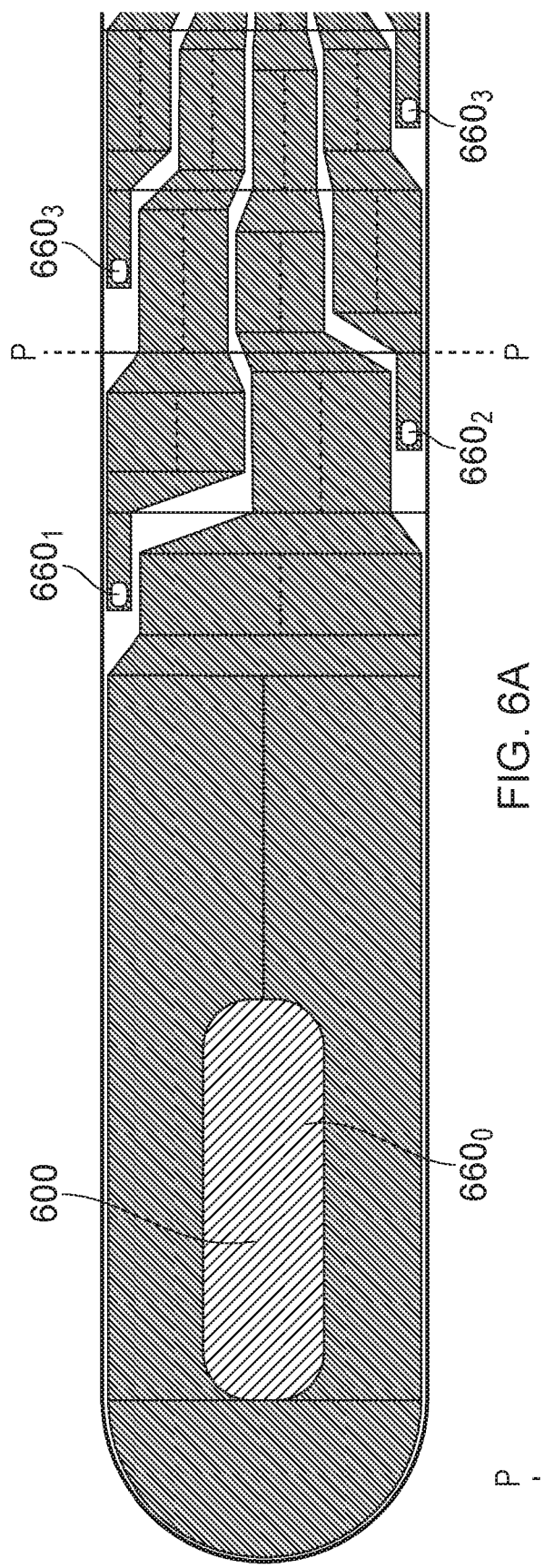
FIG. 6 illustrates different regions of electrode tracks as they extend along a support.
Figure 6C:
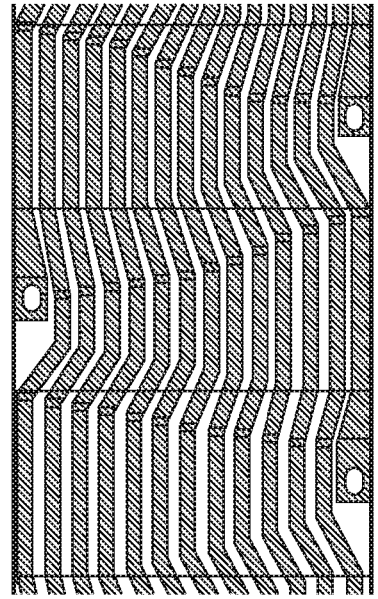
Figure 6B:
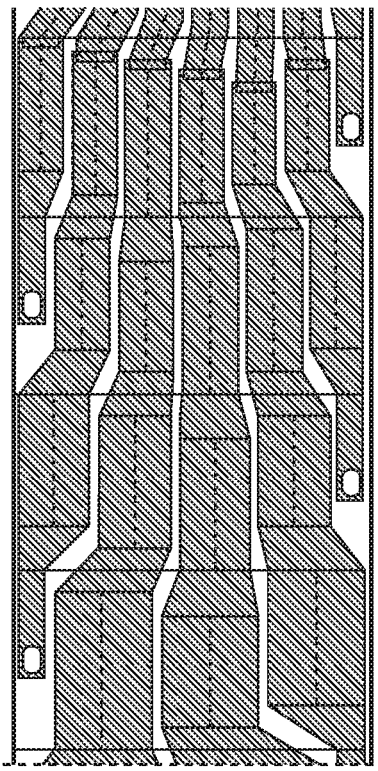
Figure 6D:
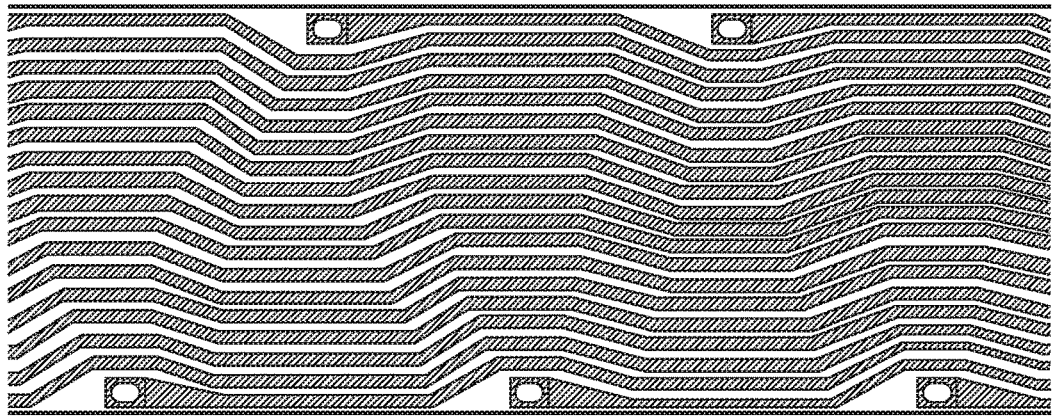
Figure 6E:
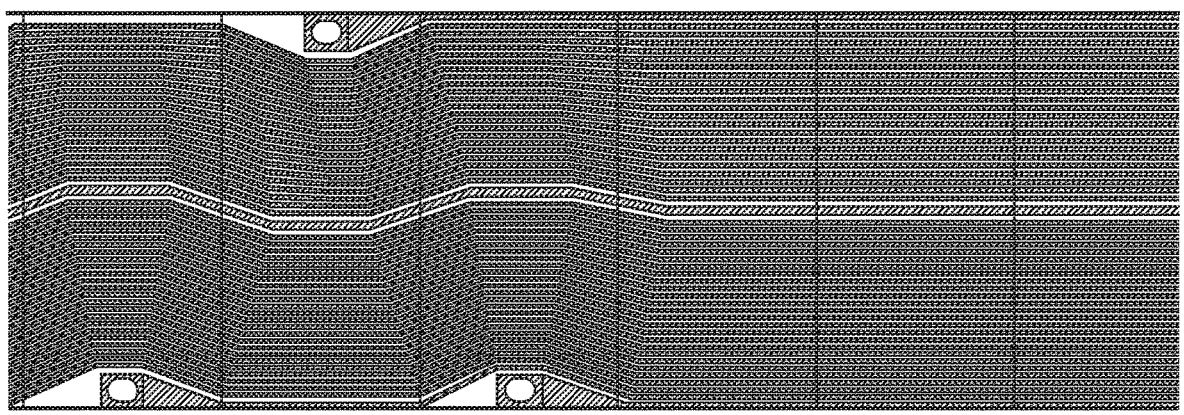

FIG. 5 helps illustrate how the electrode tracks may be supported by the substrate in more detail. In particular FIG. 5 helps illustrate the very end 400 of the narrowed neck part 260 of the substrate. As shown in FIG. 5 a reference electrode track 500 is formed on the substrate material 510. Also multiple sensing electrode tracks $520_{1-n}$ are formed adjacent to one another. Each electrode track is formed via a deposition/lithographic process as a thin metallised or other electrically conductive material pathway on a substrate. Aptly the electrode material is an etched metallic deposition element. The reference electrode track 500 illustrated in FIG. 5 provides a reference electrode for the sensor. It will be appreciated that alternatively an external reference electrode can be applied to the skin of a subject/patient (or other location) in which case a reference electrode track is not needed on the needle/substrate. The reference electrode has an enlarged end 505 which then narrows via one or more neck region 530 to a longitudinally extending portion of the electrode track. This longitudinally extending part of the reference track 540 is illustrated in FIG. 5 as running off to the right hand side of the figure (from there the track extends to a bond pad/connection pad at the other end of the substrate).

FIG. 5 thus helps illustrate how a substrate has a cross section (corresponding in plan view to the whole of the figure) with metallised or electrically conductive tracks formed selectively over selected parts of that substrate. The whole substrate is provided by a base substrate layer on which the tracks are deposited during manufacture (see later) and a cover substrate layer which over lies the base substrate layer (and thus the tracks on it). The whole substrate provides a neutral insulating envelope around the tracks leaving small access holes for sensing where the tracks are revealed. Aptly the substrate base layer and cover layer are a flexible parylene-C layer. Apertures $560_{0-7}$ are shown as being formed in the overlying cover substrate layer. As illustrated in FIG. 5 the centre of the end of the reference electrode is in register with a relatively large open area aperture $560_0$. The next electrode along (taken from the left hand side/end 400 of the substrate) is an electrode formed by a respective conductive electrode track $520_1$ which again is overlain by an insulating layer but which has an aperture $560_1$ formed in a region overlying an end of a sensing track portion of the electrode track. The opening in the overlying layer forms a sensing (or recording) surface region for that particular electrode. Each electrode track has a respective end and a respective opening is formed in the overlying insulating layer in register with a region of the sensing end. Many sensing points can thus be provided along the narrowed neck length N1 of the substrate with electrode tracks becoming progressively narrower and narrower in cross section so as to ensure that many electrode tracks are provided, each with a respective sensing point, by the time the tracks reach towards the flared out shoulder region 420 of the substrate.

FIG. 5 thus illustrates eight apertures in an insulating layer which provide access in use to surrounding tissue of a patient when the substrate, duly secured to a needle, is pierced into the patient. An aperture of the insulating layer provides access to an end of the reference electrode which, as shown in FIG. 5 is a central electrode extending from the end of the substrate neck portion via a long electrode track. It will be appreciated that a reference electrode does not need to be a central electrode in the multiple side-by-side array of electrodes. Likewise further apertures $560_{1-7}$ provide sensing regions for the other electrode tracks. As illustrated in FIG. 5 adjacent sensing points are separated by a predetermined distance z in an axial direction along the substrate. The sensing distance can be selected according to use and according to the expected distance between key body component parts such as nerves or muscle strands or the like. Apertures in the enveloping substrate around the tracks can have any shape or size that permits localised conditions in a patient to be communicated.

FIG. 6 (FIGS. 6A to 6E) illustrates a similar substrate to that shown in FIG. 5 but illustrates different regions along the length of the narrowed neck of the substrate. For example FIG. 6a illustrates the substrate end which then runs in to FIG. 6B. It will be appreciated that FIG. 6B illustrates the electrodes at point P along the length of the electrodes shown in FIG. 6A. As will be appreciated as more and more sensing points are provided along the substrate the width of each electrode track is narrowed so that all electrode tracks can be accommodated in a spaced apart manner across the common width of the substrate so that activity experienced at each individual sensing point associated with each independent electrode track can be communicated effectively.

FIG. 7 illustrates how the density of electrode tracks increases towards the wider end of the substrate as the electrode tracks extend longitudinally along the substrate. It is to be noted that the distance z by which the sensing regions are separated for adjacent sensing points remains constant despite the fact that the width of each electrode track is diminished the further away one goes from the tip of the substrate. As illustrated in FIG. 7 each electrode track comprises a connection track portion which extends substantially parallel with an axis of the needle shaft and the substrate, and that is spaced apart from one or more adjacent connection tracks. Furthermore each electrode track includes a sensing track portion which is at an end of the electrode track and which is overlaid to some extent by a respective sensing aperture. FIG. 7 helps illustrate how all of the electrode tracks can be made to zig-zag to make room for each sensing track portion on opposed edges of the substrate. Each electrode track thus has a zig-zag-shaped connection track that extends in a nested, spaced apart, configuration with at least one adjacent zig-zag-shaped connection track. It will be appreciated that other nesting/electrode track route designs may be utilised according to certain other embodiments of the present invention.

Figure 8:
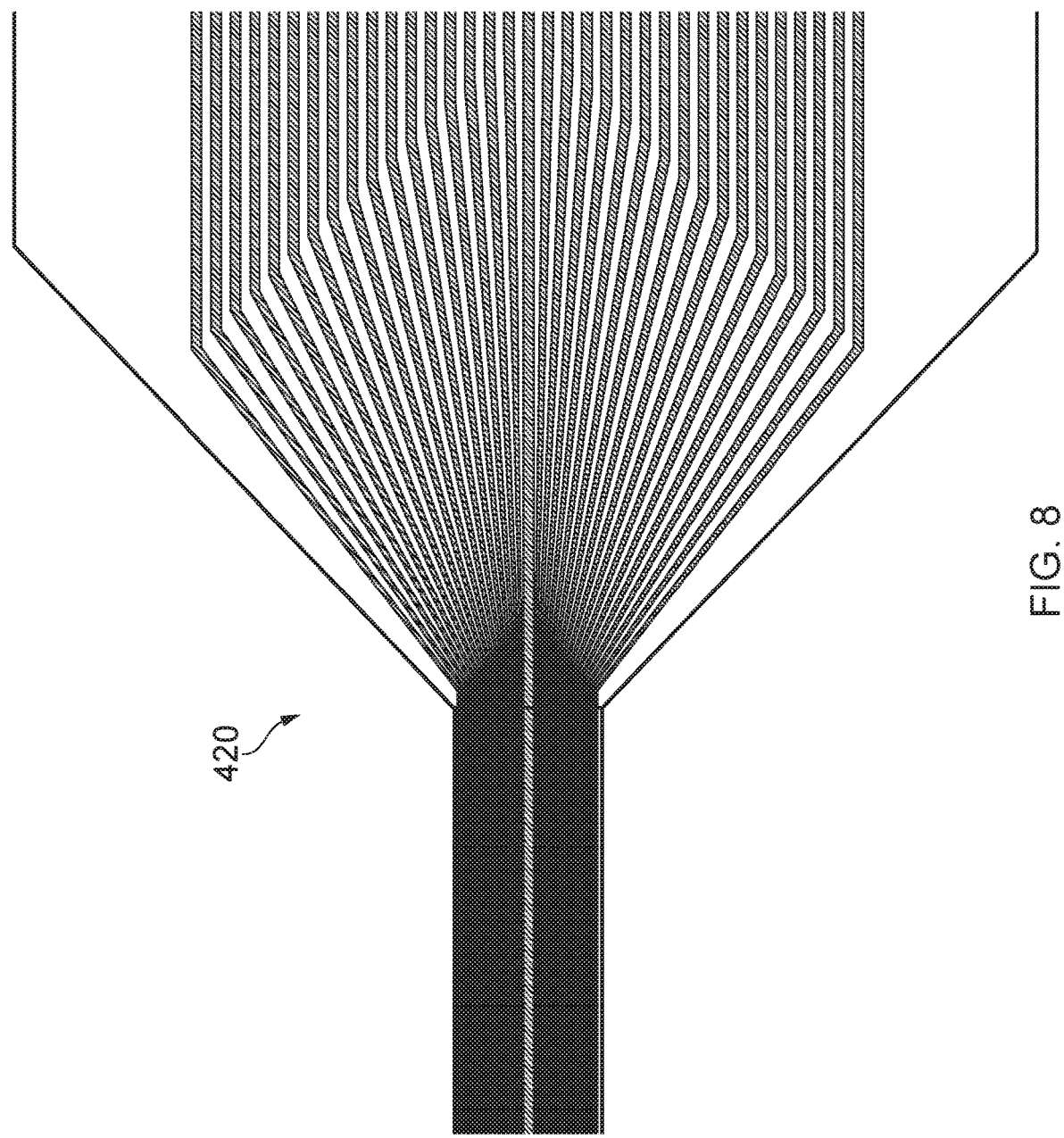
FIG. 8 illustrates a shoulder region of a supporting substrate and how electrode tracks fan out from a narrow neck towards contact pads.

FIG. 8 helps illustrate the shoulder or intermediate region 420 of the substrate in more detail and illustrates how a large number of spaced apart electrode tracks extend longitudinally along the substrate at the end of the narrow neck part of the substrate distal from the narrow end 400 of the substrate. As each track reaches the shoulder region 420 of the substrate the tracks gradually fan out so as to become more spaced apart so that the electrode tracks themselves can increase in width. These tracks are then each independently connected to a respective bond pad (not shown) to which connection can be made to sensing circuitry/processors in a conventional manner.

According to certain embodiments of the present invention the recording surfaces of the electrodes are disposed on the needle in a preselected layout that allows for accurate localization of the muscle fibers within the muscle. In order to localize (that is to say determine a location of) a specific fiber certain embodiments of the invention make use of a suitable model/relationship for the degradation of muscle fiber amplitude with distance. Aptly this may be modelled using an exponential function. An example of a model that may be utilised is Gydikov, A. and Gatev, P., 1982. Human single muscle fiber potentials at different radial distances from the fibers determined by a method of location Experimental neurology, 76(1), pp. 25-34. Such a function is symmetrical, i.e. it will produce the same result in all directions given the same distance from the recording surface. Because a fiber sits at different distances from all the electrode recording areas, it will appear with different amplitudes on different electrodes. This change in amplitude can be used to help localize the fiber position in reference to the needle.

Due to the symmetry of the exponential function, it is conventionally challenging for any localization algorithm to predict on which side of the needle the fiber is. Conventional probes with a single row of electrode sensing/recording regions would suffer from this very problem. To break this symmetry and to help facilitate an accurate localization on both sides of the needle certain embodiments of the present invention utilise electrodes so that they are laid in a pattern. Aptly using two (or more) parallel arrays of electrode recording surfaces. Because of this design two fibers located on equal distances to the needle but on opposite sides will have two different profiles on the needle, which guarantees accurate localization. It will be appreciated that having electrode sensing regions that are not aligned in one common linear array is sufficient to be able to resolve the localization problem so that a scattered array of electrode recording surfaces or curved line/s of electrode recording surfaces may be utilised.

Aptly the distances between electrode recording surface regions in each row and between each row may be the same or may be selected to balance between maximum coverage of the muscle, localization accuracy, and ability to manufacture the electrodes. Aptly the size of a single electrode recording surface region is chosen as well to cover a 1 mm^2 area around the needle in both directions (up and down). Aptly the overall coverage area may be around 12×2 mm^2 which is selected to cover most the muscles of interest. Other sizes of electrode sensing region and overall coverage could of course be chosen according to use. Aptly certain embodiments of the present invention have the ability to provide maximal, continuous coverage of the muscle with high localization accuracy in a 2D space.

FIG. 9 (FIGS. 9A to 9Q) helps illustrate a method of manufacturing the multi-contact electrodes and flexible substrate previously described. As illustrated in FIG. 9A a carrier wafer 900 is provided. This may optionally be a commercial 3" silicon wafer. This wafer undergoes a solvent clean process in which the carrier silicon wafer is immersed in N-methyl-2-pyrrolidone (NMP) for 5 minutes to remove oils or organic residues from the surface. This is followed by immersion in isopropanol (IPA) for 5 minutes to remove any NMP residues. Subsequently the wafer is rinsed in de-ionised (DI) water for 2-3 minutes to remove any IPA. The wafer is then dried with a nitrogen jet gun followed by 10 minutes resting at 100° C. in an oven. This provides a clean silicon wafer.

Figure 9A:
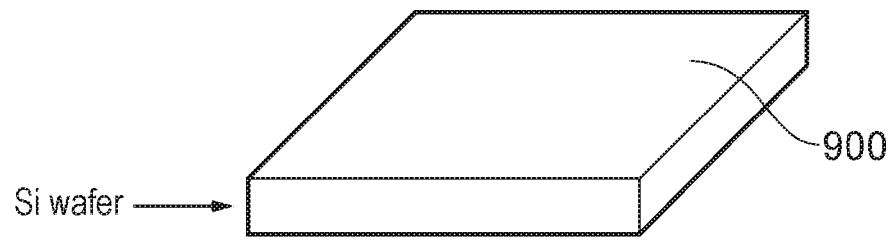
FIG. 9 illustrates manufacturing steps for manufacturing a substrate with electrode tracks.
Figure 9B:
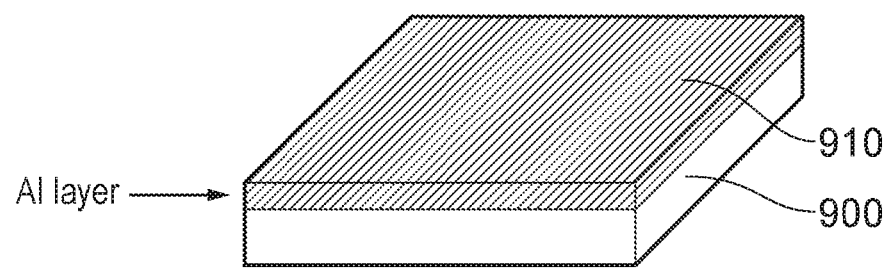

As illustrated in FIG. 9B a sacrificial aluminium layer 910 is then provided on the silicon wafer. Aptly a 300 nm-thick layer of aluminium is deposited as a sacrificial layer using an e-beam evaporation technique. For example a BOC-Edwards auto electron beam evaporation technique can be utilised at a base pressure of $2\times10^{-6}$ mbar and at a deposition rate of about around 0.25 nm/s. The aluminium layer is then cleaned using a solvent clean process to provide a clean wafer and Al layer.

Figure 9C:
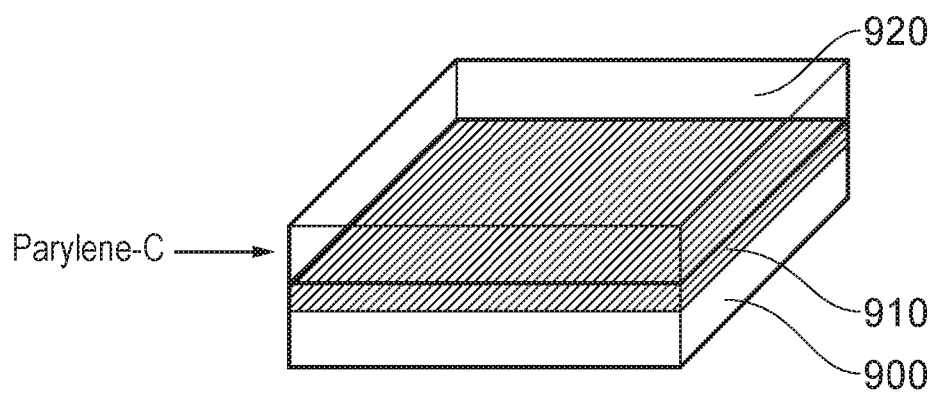

As illustrated in FIG. 9C a 10 µm thick layer 920 of parylene-C is then deposited using a chemical vapour deposition (CVD) step. Other thicknesses can of course be utilised. A solvent cleaning process as described above with respect to FIG. 9A is then applied to create a clean wafer-aluminium layer-parylene-C sandwich.

Figure 9D:
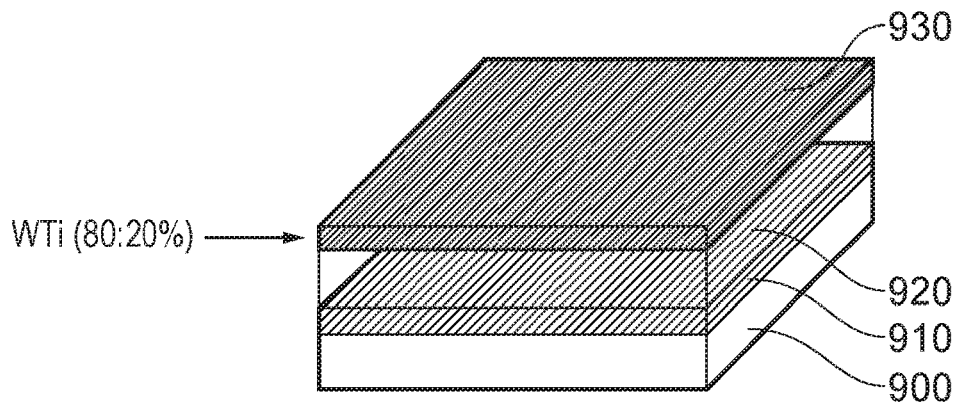

FIG. 9D helps illustrate a tungsten titanium deposition step in which a tungsten titanium layer 930 is provided over the parylene-C deposition layer.

During the tungsten titanium deposition step shown in FIG. 9D a 1 µm thick film of W:Ti (80:20%) alloy is deposited by a sputtering process. For example a Kurt J. Lesker PVD 75 vacuum deposition system can be utilised using a 99.9% pure W:Ti target from Pi-Kem. Chamber environment may optionally be maintained using a constant argon gas flow of 15 sccm and a pressure of 19 mTorr. The power of the sputtering system is around 100 W. A solvent clean process is carried out. Other thicknesses or other materials could of course be utilised.

Figure 9E:
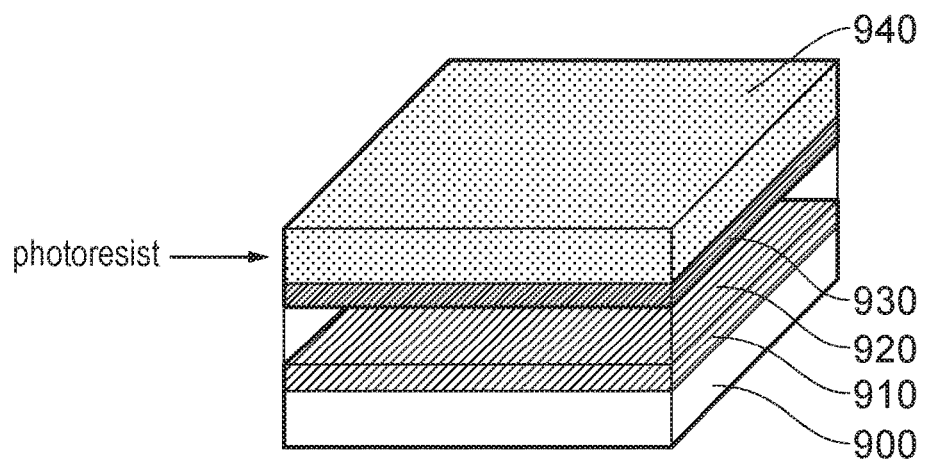

FIG. 9E helps illustrate how a layer of photoresist 940 is then provided over the tungsten titanium layer 930. Subsequent to any wafer cool down to room temperature after a dry convection oven step used to clean the tungsten titanium layer an Az5214E photoresist layer 945 from Micro Chemicals is deposited on the WTi surface and spun for (i) 10 seconds at 500 rpm and then (ii) 40 seconds at 4000 rpm to form a uniform photoresist layer of thickness about around 1.5 µm covering the entire tungsten titanium surface. The photoresist is then baked for 15 minutes at 90° C. in a convection oven to create a hardened photoresist layer.

Figure 9F:
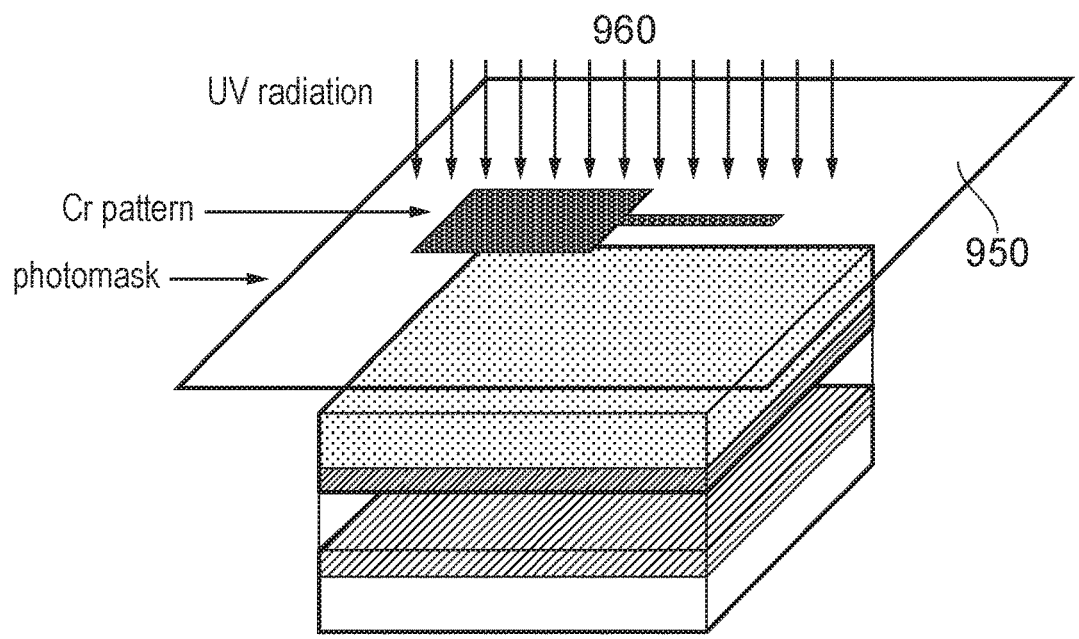

FIG. 9F helps illustrate how a physical mask layer 950 is overlaid over the photoresist layer 940. Aptly the mask layer is a quartz glass with chrome patterning or the like. Aptly a Karl Suss MJB-3 mask liner is used to expose photoresist under the photo mask 950 to UV light 960 at an intensity of about around 10 mW/cm² for 14 seconds.

Figure 9G:
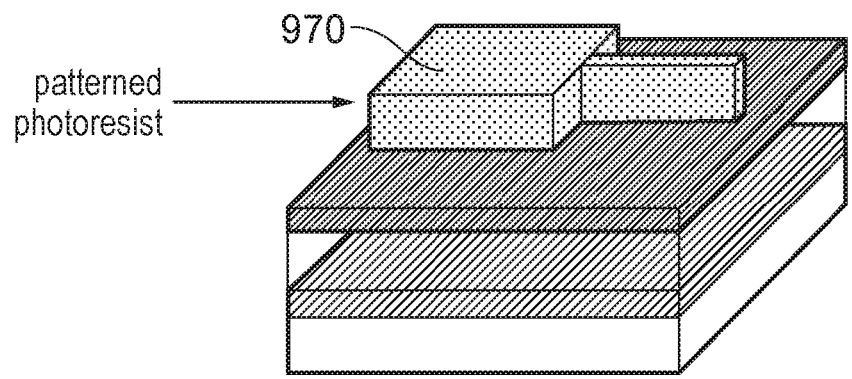

FIG. 9G helps illustrate how a developer can be then utilised to develop the patterned photoresist layer. Aptly developer AZ-326 MIF from Micro Chemicals is used to develop the photoresist. The developing time is selectable. Aptly the developing time is between 20-30 seconds. The patterned photoresist is then hard baked for 30 minutes at 120° C. in a convection oven to create a patterned photoresist 970.

Figure 9H:
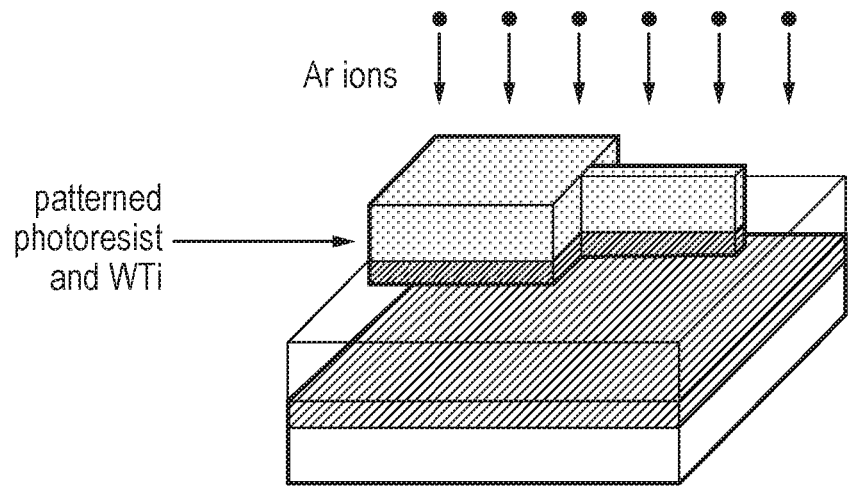
Figure 9I:
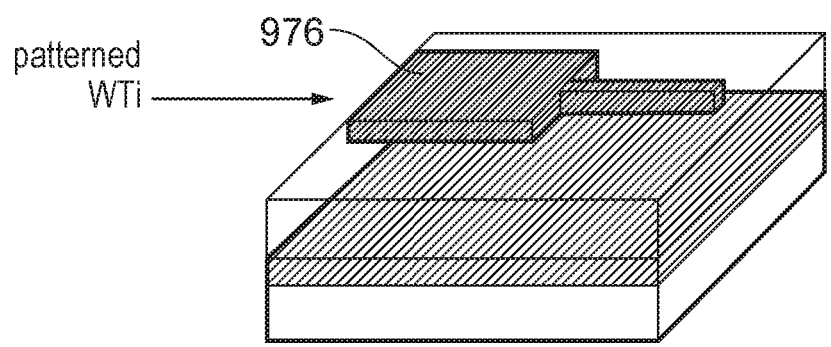

FIG. 9H helps illustrate how the hardened photoresist is used as a mask to pattern the underlying tungsten titanium layer by a reactive ions etch (RIE) process. Aptly this step is carried out no longer than 5 minutes after having removed the wafer from the oven utilised to hard bake the patterned photoresist. Aptly RIE is carried out in a Plasma-Therm 790 machine at a pressure of 150 mTorr and power of 175 W. The gas mixture in the chamber is $SF^6$(40%)/Ar(60%). The plasma etch is run for about around 6 minutes. The etch rate for WTi under these parameters is about around 200 nm/min which helps ensure that the complete removal of exposed WTi (no photoresist mask) areas and also over etches about around 500 nm into the parylene-C layer. The parylene-C over etch helps roughen the parylene-C surface which helps improve adhesion of a second parylene-C layer. Post RIE etching the photoresist mask is removed in NMP followed by 5 minutes in IPA (the NMP immersion time is as long as necessary to fully remove the photoresist). FIG. 9I helps illustrate the patterned WTi layer 976 with the photoresist removed.

Figure 9J:
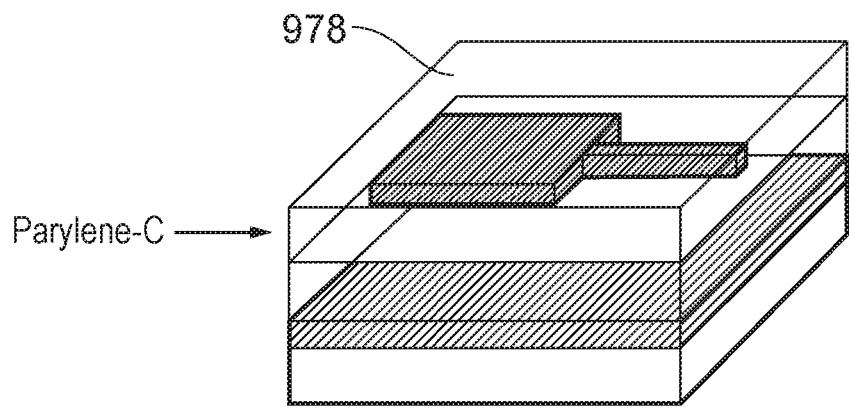

FIG. 9J helps illustrate the provision of a second parylene-C layer 978, via a similar deposition step to that previously discussed with respect to the first parylene-C layer 920, over the first parylene-C layer and the patterned WTi. The first parylene-C layer 920 and second parylene-C layer 978 together form the substrate which envelops the etched tracks of WTi. That is to say the etch pattern for the WTi is used to create the reference electrode and sensing electrode tracks previously described and that the first parylene-C layer acts as a base substrate layer and then the second parylene-C layer will cover the tracks and exposed surface of the first parylene-C layer to effectively create a shell around the electrode/sensing tracks. The following steps are utilised to then etch the parylene-C layers to create the substrate previously described and release this from the underlying silicon wafer.

Figure 9K:
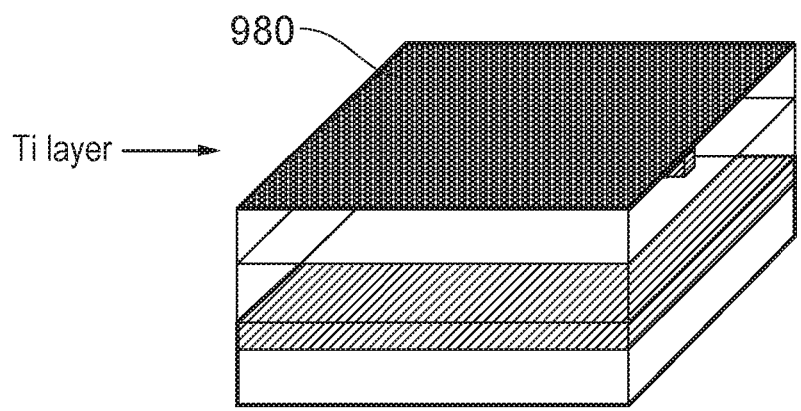

FIG. 9K illustrates how a titanium mask layer 980 is deposited over the second parylene-C deposition layer 978. A 30 nm-thick layer of Ti is deposited using a BOC-Edwards auto electron-beam apparition (E-beam) at a base pressure of $2\times10^{-6}$ mbar at a deposition rate of about 0.15 nm/s.

Figure 9L:
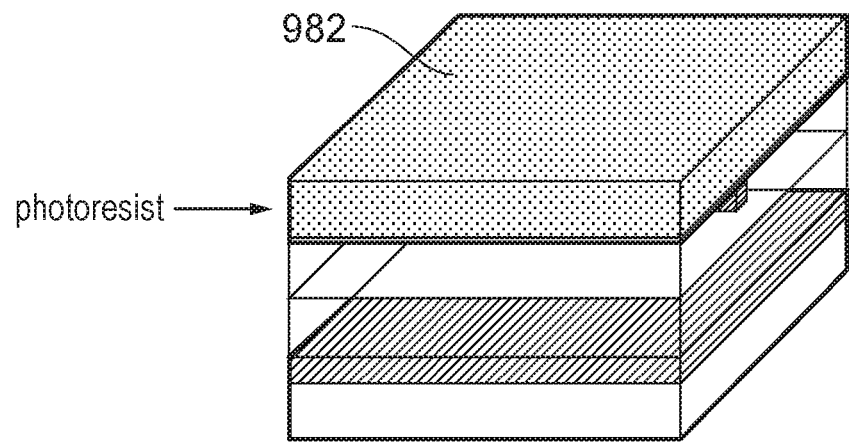

FIG. 9L helps illustrate how a further photoresist layer 982 is then provided over the titanium mask deposition layer 980. This further photoresist layer 982 is deposited and then patterned in many respects similar to previously described. Aptly AZ5214 E photoresist from Micro Chemicals is deposited and spun for (i) 10 s at 500 rpm and then (ii) 40 s at 4000 rpm to form a uniform photoresist layer at thickness about 1.5 µm covering the titanium layer 980. The photoresist is then baked for about around 15 minutes at 90° C. in a convection oven.

Figure 9M:
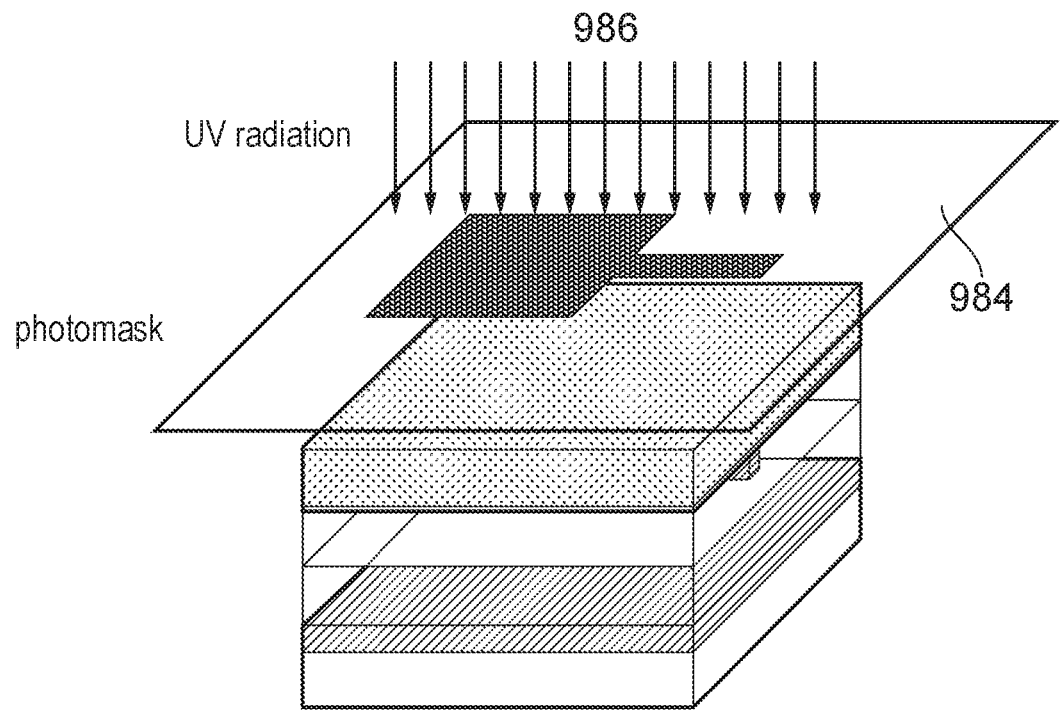

FIG. 9M illustrates how a photomask 984 is then utilised to reveal selected regions of the photoresist to UV radiation 986. Aptly a Carl Zeiss MJB-3 mask liner is used to expose the photoresist (using a photomask) to UV light at an intensity of about around 10 mW/cm² for 14 seconds. The photomask 984 illustrated in FIG. 9M has a different pattern to the photomask utilised with respect to FIG. 9F.

Figure 9N:
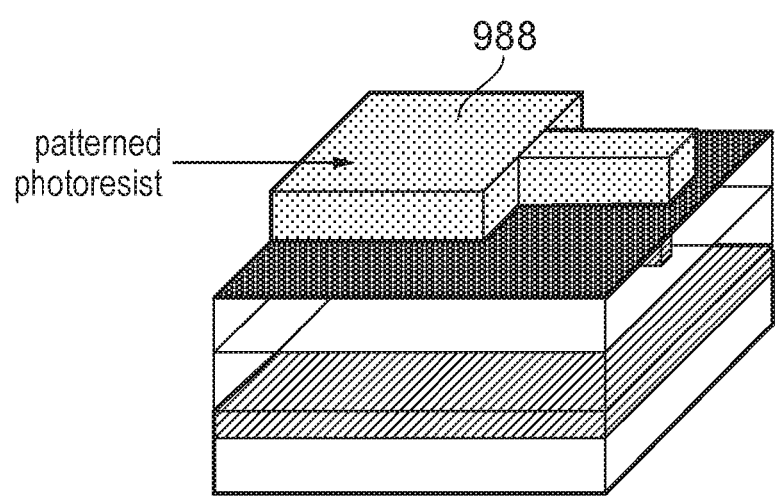

FIG. 9N illustrates how the photoresist is developed to create a patterned and hardened photoresist layer 988. Aptly developer AZ-326MIF from Micro Chemicals is used to develop the photoresist. The developing time is aptly about around 20 s to 30 s. The patterned photoresist is then hard-baked for about around 30 minutes at 115° C. in a convection oven.

Figure 9O:
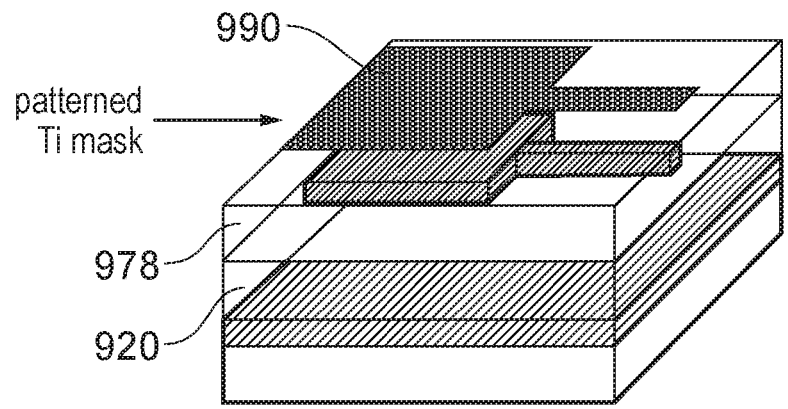

The unexposed Ti (not masked by photoresist region) is then etched in $H_2O$:HF (60:1) for about around 2 seconds. This creates a patterned titanium mask layer 990 which is illustrated in FIG. 9O. The photoresist 988 is then removed (this is illustrated in FIG. 9O) in NMP followed by a 5 minutes in IPA (the NMP immersion time is as long as necessary to fully remove the photoresist).

Figure 9P:
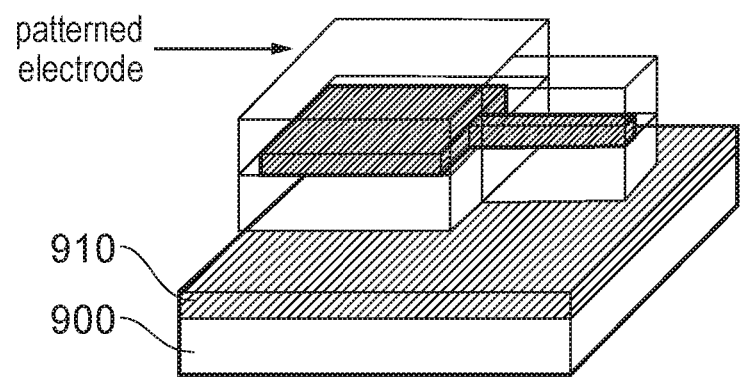

FIG. 9P illustrates RIE etching of the base parylene-C layer 920 and cover parylene-C layer 978 using the patterned Ti mask 990. RIE etching of the parylene-C is carried out in a Plasma-Therm 790 machine at a pressure of 50 mTorr and a power of about around 200 W. The gas mixture in the chamber is provided as substantially only oxygen. The plasma etch is run for a total time of about around 90 minutes in two stages. The etch rate for parylene-C under these parameters is about 300 nm/min. After a first etch step of around 60 minutes the wafer is taken out of the RIE chamber for inspection. Any residues on the surface are blown off using a nitrogen jet gun. A second etch step of about around 30 minutes completes the parylene-C etch. The remaining Ti mask 990 is then removed in $H_2O$:HF (30:1) for about around 2 seconds. After the Ti mask removal the wafer is rinsed in deionised water for several minutes and then dried with a nitrogen jet gun. The resultant structure is illustrated in FIG. 9P which illustrates patterned WTi in a parylene-C substrate shell on the first aluminium layer on the silicon wafer 900.

Figure 9Q:
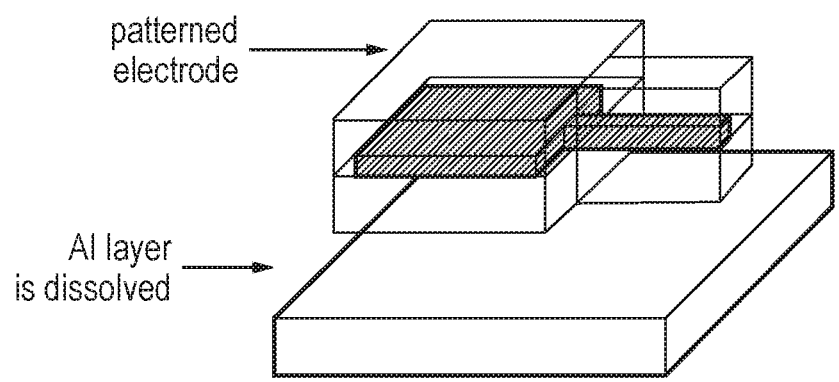

FIG. 9Q illustrates release of the substrate containing electrodes from the wafer. The electrodes with surrounding substrate are released from the carrier wafer 900 by dissolving the sacrificial aluminium layer 910 in tetra methyl ammonium hydroxide (TMAH) at about around 60° C. If after about around 5 minutes in the TMAH solution at 60° C. there are any areas still attached to the carrier wafer (i.e. the aluminium beneath has not dissolved completely) the old TMAH is disposed of and fresh TMAH is heated up to about around 60° C. in order to continue with the releasing process.

FIG. 10 illustrates the silicon wafer 900 in more detail during a process in which multiple flexible substrates supporting electrodes can be manufactured in a side-by-side arrangement prior to release of each of the separate substrate and electrode elements which can then each be independently used with a respective needle.

Figure 11:
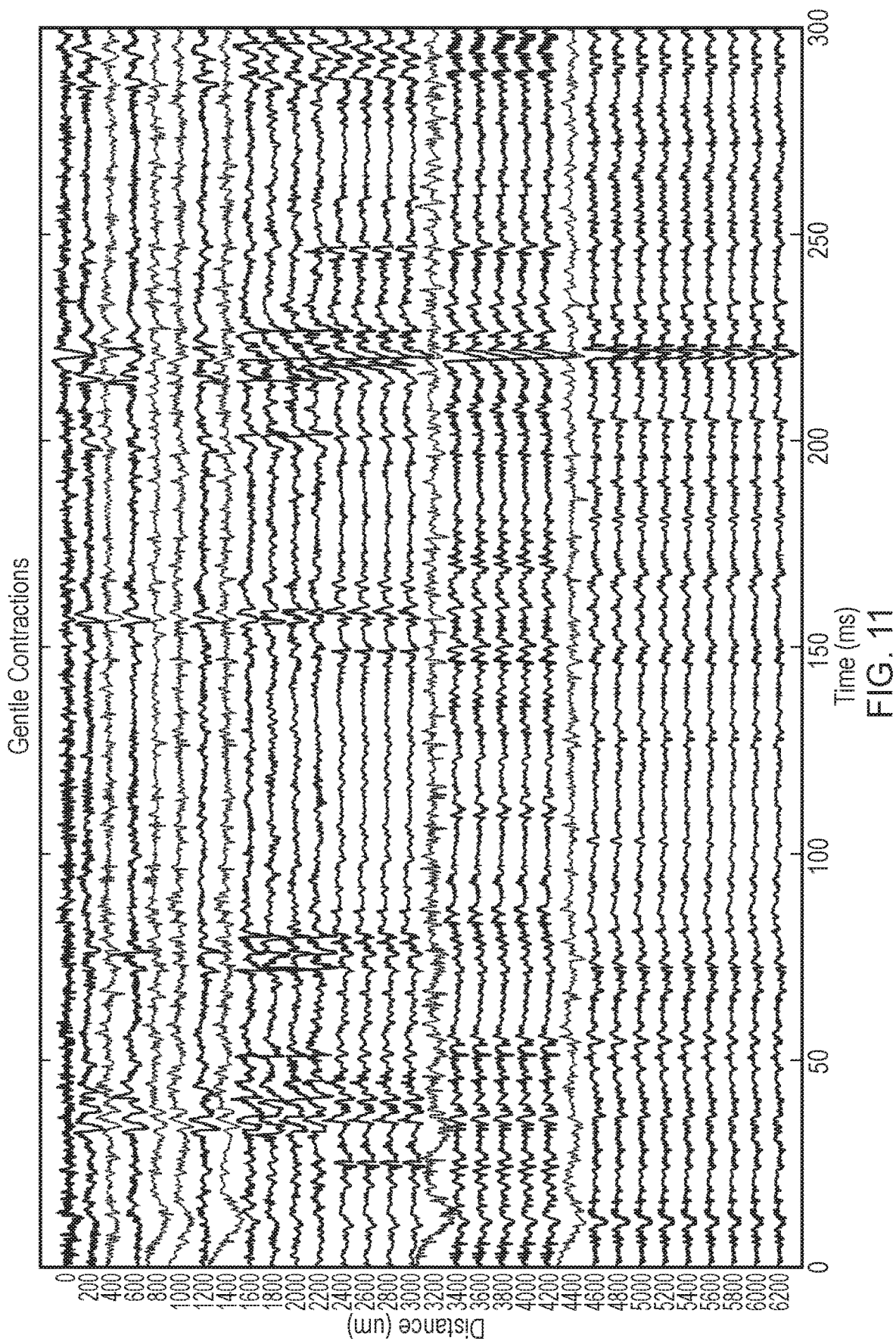
FIG. 11 illustrates a multichannel recording responsive to probe signals from a human anterior muscle.

Certain embodiments of the present invention thus enable electrodes to be fabricated on silicon wafers that are encased in a flexible bilayer of parylene-C. This is an FDA approved flexible polymer. The bilayer encased tungsten titanium electrode tracks are flexible and may be bonded to a conventional EMG needle or the like to allow penetration into human muscles. The flexible substrates can thus be utilised in an electrode diagnostic medicine technique for evaluating and recording electrical activity produced by skeletal muscles. The substrate and needle provide an electromyograph which can be utilised to record an electromyogram. The electromyograph can be utilised to detect electric potential generated by muscle cells when those cells are electrically or neurologically activated. Probe signals responsive to activity at a single needle location, but from multiple positions within the body, can be amplified using conventional technologies such as an intan multichannel amplifier which may optionally be located in the hand held unit. This may be connected in a conventional technique to a standard laptop or other processing technology. FIG. 11 illustrates a 32 channel recording obtained in 30 seconds from a human subject.

Certain embodiments of the present invention thus provide a micro-fabricated, flexible, multi-contact electrode comprising an array of many recording sites extending over a distance of two to fifteen millimetres from a piercing tip of a needle. This is comparable with the size of a human motor unit. A diameter of each recording site is only about around 25 μm. This enables recording of a cross section of a motor unit at a resolution high enough to study individual muscle fibres. The recording site is connected to a matrix of contact pads designed to match an electronic board containing read out circuitry.

According to certain embodiments of the present invention a sputtered tungsten titanium film can aptly be used to form micro contacts, connections and wires using photoli-thography and associated reactive ion etch techniques. The tungsten/titanium contact array is encapsulated between a double parylene-C (or other selected flexible inert layer material) deposited, for example, by chemical vapour deposition (CVD). The flexible electrodes are aptly fabricated on silicon wafers coated with a sacrificial aluminium or other metal layer and thereafter released subsequent to creation of electrode tracks.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An apparatus for simultaneously providing a plurality of probe response signals indicative of electrical activity at a respective plurality of locations in a patient, comprising:
   a rigid needle shaft element comprising a piercing tip; and
   a substrate, supporting a plurality of electrode tracks, secured to the needle shaft element and extending along the needle shaft element away from the piercing tip;
   wherein each electrode track extends from a sensing end region arranged for providing a respective probe response signal responsive to localised electrical activity, along a region of the substrate, to a respective bond pad connection region, and recording surface regions of the plurality of electrode tracks are spaced apart in a plurality of substantially linear spaced apart configurations, in an axial direction along the substrate;
   wherein each electrode track comprises a zig-zag shaped connection track portion which extends in a nested spaced apart configuration with at least one zig-zag shaped connection track portion of an adjacent electrode track, and the electrode tracks each become progressively narrower in cross-section moving away from the piercing tip.

2. The apparatus as claimed in claim 1 wherein in the substrate is formed from a flexible material.

3. The apparatus as claimed in claim 1, wherein:
the substrate is bent at least partially around a cylindrical outer surface of the needle shaft element.

4. The apparatus as claimed in claim 1, wherein:
the substrate is bonded to an outer surface of the needle shaft element.

5. The apparatus as claimed in claim 1, wherein:
each electrode track comprises a fan out portion that turns away from an imaginary centre line of the substrate and extends towards an edge region of the substrate from a distal end of a respective connection track portion of the electrode track towards a respective bond pad connection.

6. The apparatus as claimed in claim 1, wherein:
each electrode track comprises a sensing track portion that extends from an end of a respective connection track portion of the electrode track and is substantially aligned in a common direction with the end of the respective connection track portion and has a width greater than or less than a width of the end of the respective connection track portion, a terminal end of the sensing track portion comprising the sensing end region.

7. The apparatus as claimed in claim 1, further comprising:
at least one reference electrode track including a terminal end portion and at least one reference electrode connection track portion.

8. The apparatus as claimed in claim 1, wherein the substrate supports at least sixteen distinct spaced apart electrode tracks.

9. The apparatus as claimed in claim 1 wherein each electrode track comprises a metallic conductive pathway.

10. The apparatus as claimed in claim 9 wherein each electrode track comprises a tungsten titanium track.

11. The apparatus as claimed in claim 1 wherein the apparatus comprises an electromyography (EMG) needle.

12. The apparatus as claimed in claim 11 wherein a recording surface region of each electrode track is substantially circular and has a diameter of about around 40 to 60 µm.

13. The apparatus as claimed in claim 12, wherein:
each recording surface region of the plurality of electrode tracks are spaced apart in a respective one of two substantially linear configurations along the substrate.

14. The apparatus as claimed in claim 1 wherein the apparatus comprises a microneurography needle.

15. A method of diagnosing at least one disease in a patient, comprising:
using the apparatus of claim 1, urging the rigid needle shaft element through the skin of a patient; and
via the plurality of electrode tracks, simultaneously providing a plurality of probe response signals each indicative of electrical activity at a respective one of a plurality of locations in the patient.

16. The method as claimed in claim 15, further comprising:
displaying at least one output trace on a display responsive to the probe response signal; and
responsive to the output trace, determining a likelihood of one or more diseases.

17. The method as claimed in claim 15, further comprising:
providing a 2-D image of said probe signal in real time.

18. The method as claimed in claim 15, further comprising:
a) providing an image of a motor unit morphology and/or motor unit stability responsive to the probe signals;
b) simultaneously providing jitter recordings from multiple fibres in a patient at need location site, and/or;
c) simultaneously recording a measured voltage from a plurality of sub locations in the patient at each needle location site.

* * * * *